United States Patent [19]

Broggi et al.

[11] 4,139,702
[45] Feb. 13, 1979

[54] PROCESS FOR PREPARING CEPHALOSPORINES

[75] Inventors: Renato Broggi; Marco Falciani, both of Milan, Italy

[73] Assignee: DOBFAR S.p.A., Milan, Italy

[21] Appl. No.: 859,526

[22] Filed: Dec. 12, 1977

[30] Foreign Application Priority Data

Dec. 16, 1976 [IT] Italy ............................... 30482 A/76

[51] Int. Cl.² ........................................... C07D 501/06
[52] U.S. Cl. ...................................... 544/27; 544/28; 544/30
[58] Field of Search .......................... 544/30, 27, 28

[56] References Cited

U.S. PATENT DOCUMENTS

| 3,988,326 | 10/1976 | Seki et al. | 544/30 |
| 4,029,806 | 6/1977 | Krohn et al. | 544/30 |
| 4,051,131 | 9/1977 | Robinson | 544/30 |

Primary Examiner—Nicholas S. Rizzo
Attorney, Agent, or Firm—Oblon, Fisher, Spivak, McClelland & Maier

[57] ABSTRACT

A process for preparing cephalosporines in which a cephalosporanic derivative is treated with a polar solvent, then with an organic base to give a mixture which is cooled at a temperature lower than −25° C. A cyclic derivative of boron is added to the mixture and the temperature is increased to about 0° C. An intermediate compound is formed which by treatment first with an acylating agent and then with a mixture of water and alcohol provides a solution containing cephalosporines.

9 Claims, No Drawings

PROCESS FOR PREPARING CEPHALOSPORINES

This invention relates to a process for preparing cephalosporines.

In preparing cephalosporines, it is well known that several processes can be followed, such as those starting from 7ADCA, 7ACA and derivatives of 7ACA, more particularly from compounds having the formula

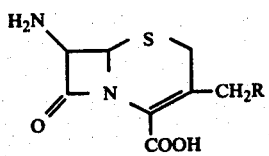

wherein R is —H, —OCOCH$_3$,

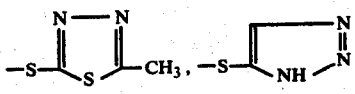

It is the common characteristic of these processes to steadily protect by protecting groups (for example, paranitrobenzyl, paramethoxybenzyl, trichloroethyl radicals) the carboxyl group during synthesis with acylating agents: these protecting groups are then removed by chemical hydrogenating reactions or with zinc and acids. Such processes are disclosed, for example, in Belgian Patents No. 745,845 and No. 777,789.

According to further known processes, however similar to those above mentioned, during synthesis with acylating agents, the carboxyl group of the cephalosporanic derivative is weakily protected with trimethylsilyl radical which is then removed by simple aqueous hydrolysis: in this case, in order to capture the mineral acidity from the acylating agent, the use should be resorted to of an organic base which, being hardly removable, would pollute the quality of the finished product. A process of this type is disclosed in U.S. Pat. No. 3,694,437, Dutch Patent No. 7,304,227 and German Patent No. 2,364,192.

It is the object of the present invention to provide a process for preparing cephalosporines, which can be readily and simply put into practice, without requiring to resort to the use of organic bases or chemical reactions to remove the protection of the carboxyl group of the cephalosporanic derivative.

These and still further objects are attained in a process, in which a cephalosporanic derivative having the formula

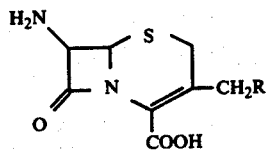

(I)

wherein R is —H, —OCOCH$_3$,

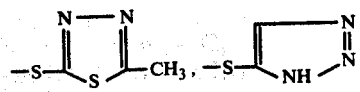

is treated at room temperature with a polar anhydrous organic solvent selected from the group consisting of acetonitrile, tetrahydrofuran, methylene chloride, chloroform, then adding a tertiary or secondary organic base selected from the group consisting of dialkylamines and trialkylamines, the process being characterized in that the resulting mixture is cooled to a temperature of between −45° C. and −25° C. and adding thereto a cyclic derivative of boron, as selected from the group consisting of ethylenchloroboronate, propylenchloroboronate and phenylenchloroboronate, in an amount of at least 2 moles for each mole of the starting cephalosporanic derivative, raising the temperature to about 0° C., thus forming an intermediate compound having the formula

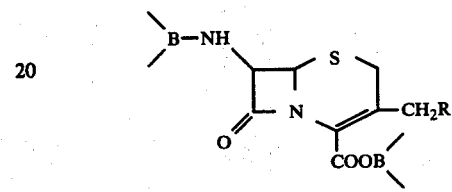

(II)

wherein R is as above defined, adding at a temperature of between −10° ÷ 0° an acylating agent selected from the group consisting of D(—)α-amino-α-phenylacetic acid chloride hydrochloride, D(—)-α-amino-(1,4-cyclohexadienyl) acetic acid chloride hydrochloride, D(—)-α-amino-parahydroxy-α-phenylacetic acid chloride hydrochloride, 1H-tetra-azolylacetic acid chloride, 4-(pyridylthio)-acetic acid chloride hydrochloride, and 2-thienylacetic acid chloride, finally adding at the completion of acetylation reaction a mixture of water and hydrosoluble alcohol to provide an aqueous solution, from which cephalosporine is isolated by known techniques.

The above mentioned intermediate compound can be isolated from its forming reaction medium, and then used for completing the reaction, or can be left in the reaction medium without any isolation to complete a continuous process.

The above cited cyclic derivatives of boron are per se well known and, for example, can be prepared according to the procedure disclosed by J. A. Blau in J. Chem. Soc. 4116 (1957), wherein the preparation of ethylenchloroboronate, that is 2-chloro-1,3,2-dioxaborinane is shown.

In order that the practical methods and characteristics of the process according to the present invention be more clearly understood, some exemplary embodiments of the invention will now be described, as given by mere way of unrestricted example.

EXAMPLE 1

PREPARATION IN TWO STEPS OF 7-[D(—)-α-AMINO-α-PHENYLACETAMIDO] DESACETOXY CEPHALOSPORANIC ACID MONOHYDRATE (cephalexinemonohydrate).

6 g 7-amino desacetoxy cephalosporanic acid (7-ADCA) were sespended in 90 ml anhydrous tetrahydrophuran. At room temperature, 7.8 ml triethylamine were dropwise added to the suspension, thus obtaining a nearly complete dissolution of 7-ADCA. The mixture was cooled to −35° C., then pouring in 30 minutes 48.9 ml of 1.2 molar solution of ethylene chloroboronate in tetrahydrofuran. The exothermic behaviour of the reaction was controlled, then gradually heating to 0° C. in 2 hours and finally to +15° C.

The mixture containing suspended triethylamine hydrochloride was vacuum evaporated to 50 ml at 20° C. The precipitate was filtered by washing with a small amount of tetrahydrofuran and again evaporated to syrup consistency, suspended with hexane to collect the solid, and filtered, obtaining 10.4 g of a clear amorphous powder comprising a novel molecule, intermediate in cephalosporine preparation, and which is 1,3,2-dioxaboranyl-7-(1,3,2-dioxaboran-2-yl-amino) desacetoxy cephalosporonate. In the from of amorphous powder, 10.2 g of this novel molecule were solved in 100 ml anhydrous methylene chloride. The solution was cooled to −5° C., and added with 5.7 g D(−)-α-amino-α-phenylacetic acid chloride hydrochloride.

The exothermic behaviour of the reaction was controlled, then gradually heating to +25° C. in 2 hours. The product was cooled to 0° C., then pouring 90 ml of an aqueous 50% methanol solution. The product was allowed to rest and the phases separated. The organic phase was washed with 30 ml water.

The combined aqueous extracts were highly acidic and contain the salified product as hydrochloride. The solution was treated with decolouring carbon and dicalite, then filtered and added with 15 ml acetone. With a solution of ammonium hydroxide pH was brought to 4.2 and a white precipitate was obtained.

After filtering, washing with water and acetone, the product was vacuum died at 40° C., obtaining 6.9 g 97.5% 7-[D(−)-α-amino-α-phenylacetamido]-desacetoxy cephalosporanic acid monohydrate: m.p. 182° C. (with decomposition), specific rotation $[\alpha]_D = 151°$ on dry, $H_2O$ (K.F.) = 7.1%.

EXAMPLE 2

PREPARATION OF 7-[D(−)-α-AMINO-α-PHENYLACETAMIDO]-DESACETOXY CEPHALOSPORANIC ACID MONOHYDRATE (cephalexin monohydrate).

10.7 g 7-ADCA were suspended in 120 ml methylene chloride. 13.9 ml triethylamine were poured into the suspension, then stirring at room temperature. The mixture was cooled to −30° C. and dropwise added with 92.5 ml of a 1.1 molar solution of 2-chloro-1,3,2-dioxaborinane in methylene chloride. The exothermic behaviour of the reaction was controlled, then heating to −10° C. The mixture was portion added with 12.5 g D(−)-α-amino-α-phenylacetic acid hydrochloride chloride. The mixture was held at −10° C. for 30 minutes, then the temperature was gradually increased to +15° C. in 1.5 hours. After cooling to 0° C., 80 ml of an aqueous 50% methanol solution were poured into the mixture, then allowed to decant, and the phases were separated. The organic phase was washed with 30 ml water. The combined aqueous extracts were treated with decolouring carbon. The product was filtered and the filtrate added with 40 ml acetone. With a solution of ammonium hyroxide pH was brought to 4.2. The product was allowed to crystallize at 0° C. for 2 hours and filtered, washing with water and acetone. The product was vacuum dried at 40° C., obtaining 12.9 g 7-[D(−)-α-amino-α-phenylacetamido] desacetoxy cephalosporanic acid, m.p. 182° C., 97.9% purity, specific rotation $[\alpha]_D = +151.5°$ on dry, $H_2O$ (K.F.) = 6.9%.

EXAMPLE 3

PREPARATION OF 7-[D(−)-α-AMINO-(1,4-CYCLOHEXADIENYL ACETAMIDO] DESACETOXY CEPHALOSPORANIC ACID MONOHYDRATE (cephradine monohydrate).

In accordance with the procedure of Example 2 and the amounts therein shown, starting from 10.7 g 7-ADCA and ethylene chloroboronate, a solution of 1,3,2-dioxaboranil-7(1,3,2-dioxaboran-2-yl-amino) desacetoxy cephalosporonate in methylene chloride was prepared.

The mixture was heated from −35° to −5° and portion added with 12.7 g D(−)-α-amino-α-(1,4-cyclohexadienyl) acetic acid chloride hydrochloride. The mixture was held at −5° C. for one hour, then gradually heated to +15° C. in 2 hours. After cooling to 0° C., 90 ml of an aqueous 50% methanol solution were poured. The mixture was allowed to decant and the phases separated. The organic phase was washed with 30 ml water. The combined aqueous extracts were treated with decolouring carbon. The product was filtered and the filtrate added with 40 ml acetone. With a solution of triethylamine pH was brought to 4.8. The product was allowed to crystallize at 0° C. for 2 hours and filtered, washing with water and isopropanol. The product was vacuum dried at 40° C., obtaining 12.1 g 7[D(−)-α-amino-α-(1,4-cyclohexadienyl) acetamido] desacetoxy cephalosporanic acid monohydrate, m.p. 184° C., 97.8% purity, $[\alpha]_D = +87.2°$ on dry, $H_2O$ (K.F.) = 7.1%.

EXAMPLE 4

PREPARATION OF 7 [D(−)-α-AMINO-PARAHYDROXY-α-PHENYLACETAMIDO]-3-[(1,2,3-triazol-5-yl-thiomethyl]-3-cefem-4-carboxylic acid (cefatrizine).

3.16 g 7-amino-3-(1,2,3-triazol-5-yl-thiomethyl)-3-cefem-4-carboxylic acid were suspended in 50 ml methylene chloride. 2.1 g triethylamine were poured into the suspension, stirring at room temperature for 30 minutes and cooling to −30° C. 21 ml of a 1,1 molar solution of 2-chloro-1,3,2-dioxaborinane in methylene chloride were poured into the mixture. The exothermic behaviour of the reaction was controlled, then heating to −5° C. The solution contained 7(1,3,2-dioxaboranyl-amino)-3(1,2,3-triazol-5-yl-thiomethyl)-3-cefem-4(1,3,2-dioxaboranyl) carboxylate. The mixture was added with 2.2 g D(−)-α-amino-parahydroxy-phenylacetic acid chloride hydrochloride, held at 0° C. for one hour and then gradually heated to +15° C. in 2 hours. After cooling to 0° C., 30 ml of an aqueous 50% methanol solution were added. The product was allowed to decant and the phases separated. The organic phase was washed with 30 ml water. The combined aqueous extracts were purified with decolouring carbon. The product was filtered and the filtrate added with 30 ml isopropanol. The pH was brought to 4.3 with triethylamine. The product was allowed to crystallize at 0° C. for one hour and filtered, washing with a small amount of water, then with methylisobutylketone and acetone.

The product was vacuum dried at 40° C., obtaining 2.9 g of a product which was identical to a standard sample of 7[D(−)-α-amino-parahydroxy-α-phenylacetamido]-3-[(1,2,3-triazol-5-yl)thiomethyl]-3-cefem-4-carboxylic acid.

EXAMPLE 5

PREPARATION OF 7-(2-CYANOACETAMIDO) CEPHALOSPORANIC ACID (cefacetryl).

2.72 g 7-amino cephalosporanic acid (7-ACA) were suspended in 50 ml methylene chloride. 2.2 g triethylamine were poured into the suspension, which was held at room temperature for 30 minutes, then cooled to −35° C. and 21 ml of a 1,1 molar solution of 2-chloro-1,3,2-dioxaborinane in methylene chloride were poured into the mixture. The exothermic behaviour of the reaction was controlled, then gradually heating to 0° C. in 2 hours. The solution contained 1,3,2-dioxaboranyl-7(1,3,2-dioxaboranyl-amino) cephalosporonate. The solution was held at 0° C. for one hour, then pouring therein 1.68 g cyanoacetic acid chloride dissolved in 10 ml methylene chloride. The mixture was held at 0° C. for 2 hours and then heated to 20° C. for 30 minutes. After cooling to 0° C., 30 ml water were poured. The mixture was allowed to decant and the phases were separated. The organic phase was treated with 35 ml of a saturated aqueous solution of sodium bicarbonate. The aqueous phase was acidified with diluted hydrochloric acid to pH 2. After vacuum evaporation at a low volume, the product was allowed to crystallize at 10° C. for 30 minutes, then filtered, washing with water and a small amount of isopropanol.

The product was vacuum dried at 40° C., obtaining 2.5 g 7-(2-cyanoacetamido) cephalosporanic acid, m.p. 170° C.

3.4 g 7-amino-3-[2-(5-methyl-1,3,4-thiadiazolil)-thiolmethl]-3-cefem-4-carboxylic acid were suspended in 70 ml chloroform. 1.6 g diethylamine were poured at room temperature. The suspension was cooled to −40° C. and 20 ml of a 1,2 molar solution of 2-chloro-1,3,2-dioxaborinane in chloroform were dropwise added. The exothermic behaviour of the reaction was controlled, then heating to −10° C. The solution contained 7-(1,3,2-dioxaboranylamino)-3-[2-(5-methyl-1,3,4-thiadiazolil) thiomethyl]-3-cefem-4-(1,3,2-dioxaboranyl) carboxylate. The mixture was added with 2.1 g 1-tetrazolilacetic acid chloride, and held at 0° C. for 2 hours, then pouring 30 ml water therein. The phases were allowed to separate. The organic phase was treated with 40 ml of a diluted solution of sodium bicarbonate. The phases were separated and the aqueous phase was acidified to pH 2 with diluted hydrochloric acid. The aqueous phase was vacuum evaporated and allowed to crystallize at 5° C. The product was filtered, washing with a saturated aqueous solution of sodium chloride and a small amount of water. The product was vacuum dried at 40° C., obtaining 2.4 g 7-(1-tetrazolilacetamido)-3-[2-(5-methyl-1,3,4-thiadiazolil)-thiomethyl]-3-cefem-4-carboxylic acid, m.p. 198° C.

EXAMPLE 6

PREPARATION OF 7-(1-TETRAZOLILACETAMIDO)-3-[2-5-METHYL-1,3,4-THIADIAZOLIL)-THIOMETHYL]-3-CEFEM-4-CARBOXYLIC ACID (cefazoline).

3.4 g 7-amino-3-[2-(5-methyl-1,3,4-thiadiazolil)-thiomethyl]-3-cefem-4-carboxylic acid were suspended in 70 ml chloroform. 1.6 g diethylamine were poured at room temperature. The suspension was cooled to −40° C. and 20 ml of a 1,2 molar solution of 2-chloro-1,3,2-dioxaborinane in chloroform were dropwise added. The exothermic behaviour of the reaction was controlled, then heating to −10° C. The solution contained 7-(1,3,2-dioxaboranylamino)-3-[2-(5-methyl-1,3,4-thiadiazolil) thiomethyl]-3-cefem-4-(1,3,2-dioxaboranyl) carboxylate. The mixture was added with 2.1 g 1-tetrazolilacetic acid chloride, and held at 0° C. for 2 hours, then pouring 30 ml water therein. The phases were allowed to separate. The organic phase was treated with 40 ml of a diluted solution of sodium bicarbonate. The phases were separated and the aqueous phase was acidified to pH 2 with diluted hydrochloric acid. The aqueous phase was vacuum evaporated and allowed to crystallize at 5° C. The product was filtered, washing with a saturated aqueous solution of sodium chloride and a small amount of water. The product was vacuum dried at 40° C., obtaining 2.4 g 7-(1-tetrazolilacetamido)-3-[2-(5-methyl-1,3,4-thiadiazolil)-thiomethyl]-3-cefem-4-carboxylic acid, m.p. 198° C.

EXAMPLE 7

PREPARATION OF 7-[α-(4-PYRIDYLTHIO)-ACETAMIDO]-CEPHALOSPORANIC ACID (cefapyrine).

5.4 g 7-ACA were suspended in 100 ml anhydrous acetonitrile. 4.5 g triethylamine were poured into the mixture at room temperature. The mixture was cooled to −25° C., then pouring therein 42 ml of a molar solution of ethylene chloroboronate in tetrahydrofuran. The mixture was held at −25° C. for 45 minutes, then heated to −5° C. At this temperature, 4.9 g 4-(pyridylthio) acetic chloride hydrochloride acid were charged, stirring for 2 hours. After heating to +5° C., 30 ml water were poured, then stirring for 30 minutes and vacuum concentrating to a small volume to syrup consistency. The mixture was suspended with 65 ml solution of sodium bicarbonate, then diluting with 100 ml water and acidifying with hydrochloric acid to pH 1.8. The aqueous solution was washed with two portions of 135 ml each of methylene chloride. The aqueous extract was brought to pH 3 with triethylamine, treated with decolouring carbon and dicalite, then filtered and the solution was slowly added with 400 ml acetone. The product was allowed to crystallize, filtered and then washed with acetone. After vacuum drying at 40° C., 4.9 g 7-[α-(4-pyridylthio)-acetamido] cephalosporanic acid were obtained.

EXAMPLE 8

PREPARATION OF 7-(2-THIENYLACETAMIDO) CEPHALOSPORANIC ACID (cefalotine).

2.72 g 7-ACA were suspended in 60 ml methylene chloride, then adding 2.2 g triethylamine. After cooling to −40° C., 21 ml of a 1,1 molar solution of ethylene chloroboronate in methylene chloride was poured into the mixture. The mixture was heated to −10° C. and 1.9 g of 2-thienylacetic acid chloride were poured into the mixture. Stirring was maintained for 2 hours at 0° C. 40 ml water were poured therein and after unmixing, the organic phase was added with a solution of sodium bicarbonate to constant pH 7.5. The phases were separated and the aqueous phase was washed with 50 ml methylene chloride. The aqueous phase was treated with decolouring carbon and dicalite. The product was filtered and after addition of 65 ml acetone the filtrate was acidified to pH 2. The product was allowed to crystallize at +5° C. for 2 hours, then filtered, washing with water and acetone. After vacuum drying at 40° C. 2.8 g 7-(2-thienylacetamido) cephalosporanic acid were obtained.

EXAMPLE 9

PREPARATION OF 7-[D(−)-α-AMINO-4-HYDROXY-PHENYLACETAMIDO] DESACETOXL CEPHALOSPORANIC ACID 2.14 g 7-ADCA were suspended in 40 ml methylene chloride. At room temperature and under stirring 2.8 ml triethylamine were poured into the suspension, the mixture was cooled to −30° C., then 18.2 ml of a 1.1 molar solution of 2-chloro-1,3,2 dioxaborinane in methylene chloride were dropwise added. The exothermic behaviour of the reaction was controlled and the temperature was increased to −12° C. Then 2.4 g D(−)-α-amino-4-hydroxy-α-phenylacetic acid chloride hydrochloride were added to the mixture, which was maintained at −10° C. for 30 minutes, then the temperature was gradually increased to +18° C. in 1.5 hours. The mixture was cooled to 0° C. and 30 ml of an aqueous 30% methanol solution were poured. The mixture was allowed to rest and the phases were separated. The aqueous layer was purified by treatment with charcoal and filter aid. The solution was filtered and a diluted solution of sodium hydroxide was added to pH 5. The crystalline mass was stirred at 0° C. for 1 hour and filtered, washing with water and acetone. The product was dried in vacuum at 35° C., thus obtaining 2.4 g 7 [D(−)-α-amino-4-hydroxyphenylacetamido] desacetoxycephalosporanic acid. m.p. +150° C., specific rotation $[\alpha]_D^{25} = +158°$ C. (C = 0,09, water)

What is claimed is:

1. A process for preparing cephalosporines which comprises treating a cephalosporanic derivative having the formula

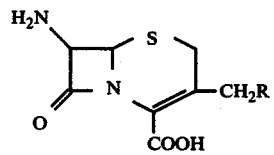

(I)

wherein R is —H, —OCOCH$_3$,

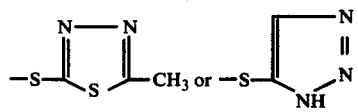

at room temperature with a polar anhydrous organic solvent selected from the group consisting of acetonitrile, tetrahydrofuran, methylene chloride, chloroform, adding a tertiary or secondary organic base selected from the group consisting of dialkylamines and trialkylamines, cooling the resulting mixture to a temperature of between −45° C. and −25° C. adding thereto a cyclic derivative of boron selected from the group consisting of ethylene chloroboronate, poppylene chlorobornate and phenylene chlorobornate, in an amount of at least about 2 moles for each mole of the starting cephalosporanic derivative, increasing the temperature to about 0° C., thus forming an intermediate compound having the partial formula

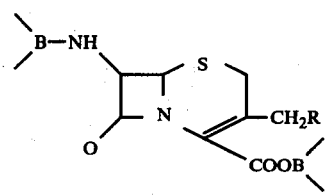

wherein R is as above defined, adding at a temperature of between −10° C. and 0° C. to carry out an acylation reaction an acylating agent selected from the group comprising D(−)-α-amino-α-phenylacetic acid chloride hydrochloride, D(−)-α-amino-(1,4-cyclohexadienyl) acetic chloride hydrochloride, D(−)-α-amino-parahydroxy-α-phenyl-acetic acid chloride hydrochloride, cyanoacetic acid chloride, 1H-tetrazolylacetic acid chloride, 4-(pyridylthio) acetic acid chloride hydrochloride, and 2-thienylacetic acid chloride, and finally adding at completion of the acylation reaction a mixture of water and hydrosoluble alcohol to provide an aqueous solution from which cephalosporine is isolated.

2. A process according to claim 1, wherein to obtain cefalexine R is —H, and the acylating agent is D(−)-α-amino-α-phenylacetic acid chloride hydrochloride.

3. A process according to claim 1, wherein to obtain cefradine R is —H and the acylating agent is D(−)-α-amino-(1,4-cyclohexadienyl) acetic chloride hydrochloride.

4. A process according to claim 1, wherein to obtain cefatrizine, R is

and the acylating agent is D(−)-α-amino-parahydroxy-phenylacetic acid chloride hydrochloride.

5. A process according to claim 1, wherein to obtain cefacetryl R is —OCOCH$_3$ and the acylating agent is cyanoacetic acid chloride.

6. A process according to claim 1, wherein to obtain cefazoline R is

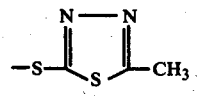

and the acylating agent is 1H-tetrazolyl-acetic acid chloride.

7. A process according to claim 1, wherein to obtain cefapyrine R is —OCOCH$_3$ and the acylating agent is 4-(pyridylthio)-acetic acid chloride.

8. A process according to claim 1, wherein to obtain cefalotine R is —OCOCH$_3$ and the acylating agent is 2-thienylacetic acid chloride.

9. A process according to claim 1, wherein to obtain 7 [D(−)-α-amino-4-hydroxyphenylacetamido] desacetoxycephalosporanic acid, R is H and the acylating agent is D(−)-α-amino-4-hydroxy-α-phenylacetic acid chloride hydrochloride.

* * * * *